United States Patent [19]
Hartlage

[11] 3,933,872
[45] Jan. 20, 1976

[54] METHOD FOR PREPARING FATTY HYDROXAMATES

[75] Inventor: James A. Hartlage, Worthington, Ohio

[73] Assignee: Ashland Oil, Inc., Ashland, Ky.

[22] Filed: Apr. 20, 1973

[21] Appl. No.: 353,166

Related U.S. Application Data

[63] Continuation-in-part of Ser. No. 10,589, Feb. 11, 1970, abandoned, which is a continuation-in-part of Ser. No. 569,850, Aug. 3, 1966, abandoned.

[52] U.S. Cl. ........ 260/404; 260/500.5; 260/501.15; 75/.5 A
[51] Int. Cl.²................... C07C 83/08; C07C 91/26
[58] Field of Search............. 260/404, 500.5, 500.15

[56] References Cited
UNITED STATES PATENTS

| | | | |
|---|---|---|---|
| 2,346,665 | 4/1944 | Cupery | 260/561 K X |
| 2,397,508 | 4/1946 | Rouault et al. | 260/500 |
| 2,733,215 | 1/1956 | Ruff | 260/404 X |
| 3,427,316 | 2/1969 | Wakeman et al. | 260/404 X |

OTHER PUBLICATIONS

Endres et al., Journ. Org. Chem., Vol. 24, pp. 1497–1501.

*Primary Examiner*—Ethel G. Love

[57] ABSTRACT

A method for the preparation of fatty hydroxamates wherein an agitated anhydrous slurry of hydroxylamine sulfate and a lower alkanol solution of a lower ester of a $C_6$–$C_{22}$ fatty acid is reacted with dimethylamine to provide the corresponding hydroxamic acid which is subsequently neutralized with dimethylamine or an alkali metal base to yield, respectively, the ammonium or alkali metal salt thereof.

7 Claims, No Drawings

METHOD FOR PREPARING FATTY HYDROXAMATES

CROSS-REFERENCE TO A RELATED APPLICATION

This application is a continuation-in-part of application Ser. No. 10,589, filed Feb. 11, 1970, which in turn is a continuation-in-part of application Ser. No. 569,850, filed on Aug. 3, 1966, both now abandoned.

BACKGROUND OF THE INVENTION

1. Field of the Invention

This invention relates to a process for preparing the alkali metal or ammonium salts of fatty hydroxamic acids.

2. Description of the Prior Art

The fatty hydroxamates to which the present invention is directed are effective reagents for carrying out a variety of hydrometallurgical operations, particularly exemplary of which is the flotation recovery of metals from oxidized minerals such as, for example, in the separation of copper from chrysocolla mineral ore.

Such hydroxamates can be readily derived by reacting hydroxylamine with a fatty acid ester to provide the corresponding hydroxamic acid which can then be neutralized with an appropriate base to obtain the hydroxamate. The foregoing procedure, however, is not adapted for the commercial production of hydroxamates since hydroxylamine in a hazardously unstable compound and thus not available for use in this form. Accordingly, hydroxylamine can only be used in any commercially adaptable process either as the sulfuric or hydrochloric acid salt thereof. The hydrochloric salt of hydroxylamine, because of its complete solubility in the polar organic solvents required for effecting the reaction concerned, is the hydroxylamine generating reagent conventionally used. Given a choice, however, one would prefer to use the sulfuric acid salt for economic reasons since the hydrochloride salt is made there from.

The drawback of employing the sulfuric acid salt of hydroxylamine in a process of the type to which this invention relates is because such salt is substantially completely insoluble in the polar organic solvents which, as mentioned above, must be used as the reaction medium in order to secure the reaction of the hydroxylamine with the fatty ester. It is nonethe less possible to carry out the underlying reaction in the presence of added water. However, this mode of operation results in a substantial formation of a soap, which not only adversely affects the yield of desired product, but also poses severe processing problems for the recovery thereof.

It is, accordingly, the object of this invention to prepare fatty acid hydroxamates using hydroxylamine sulfate as the source of hydroxylamine without undergoing the formation of soap, as is prone to occur in the prior art use of this material.

SUMMARY OF THE INVENTION

In accordance with the present invention, an improved process for the preparation of either the alkali metal or ammonium salt of a fatty hydroxamic acid is provided which comprises reacting an anhydrous slurry of hydroxylamine sulfate and a lower alkanol solution of a lower alkyl ester of a $C_6 - C_{26}$ fatty acid with dimethylamine to result in the formation of the corresponding fatty hydroxamic acid which is then neutralized with an alkali metal base or further reacted with dimethylamine to provide the dimethyl ammonium fatty hydroxamate.

The novel method of this invention for effecting the reaction between hydroxylamine and a fatty acid ester to yield the fatty hydroxamic acid can only be realized through the use of dimethylamine in the manner as aforedescribed. In the contemplated reaction system of this invention, solid hydroxylamine sulfate initially exists in contact with a polar organic solvent solution of the fatty acid ester in the form of an agitated slurry. Reacting this heterogeneous system in the presence of dimethylamine results in the sulfate salt progressively reacting therewith to generate hydroxylamine accompanied by the concomitant formation of dimethylamine sulfate, which fortuitously remains completely soluble in the organic phase along with hydroxamic acid reaction product. Upon completion of the reaction, the hydroxamic acid is neutralized either by further reacting with dimethylamine to provide the dimethyl ammonium salt or with an alkali metal hydroxide to provide the alkali metal salt thereof.

DESCRIPTION OF THE PREFERRED EMBODIMENTS

The fatty esters from whence the fatty hydroxamates are prepared in accordance with this invention include the lower alkyl esters of fatty acids containing from 6 to 26 carbon atoms, such as those found in naturally occuring fats and oils. Especially preferred from the standpoint of yielding hydroxamates having singular effectiveness as froth flotation reagents is the lower molecular weight fraction of the fatty acids occurring in coconut oil. Such acids are predominantely a mixture of $C_8 - C_{10}$ saturated linear acids. The lower alkyl esters of the aforesaid fatty acids are preferred in practicing the present invention. Exemplary of the preferred esters are those obtained by esterifying the fatty acids with either methanol, ethanol or isopropanol.

As indicated above, the contemplated inert solvent medium for carrying out the novel process of this invention is preferably an anhydrous lower alkanol. Particularly preferred among such alcohols are the $C_1 - C_3$ alkanols. The amount of alcohol that can be employed is not critical. An amount of solvent capable of providing a stirrable slurry with the hydroxylamine sulfate is generally employed. The ratio of fatty ester to the hydroxylamine sulfate is likewise not critical although it is preferred to operate with approximate equivalent proportions of these reactants.

The dimethylamine can be advantageously introduced into the reaction sphere either by bubbling same into the slurry or adding the amine as a liquid to the slurry whilst, in either mode of operation, continuously stirring the reaction mixture. Reaction temperatures are preferably ambient. Similarly, the preferred pressure conditions are ambient. Higher temperatures, however, can be used consistent with the boiling point of the selected alkanol solvent. Higher reaction temperatures, up to about 100°C., at which temperature hydroxylamine is prone to decompose, are applicable. Reaction time varies depending upon the desired extent of converting the fatty ester to the hydroxamic acid. Reaction kinetics in this instance are relatively slow and consequently as long as one to two days reaction time may be required to effect complete conversion of the fatty ester.

Upon effecting the desired degree of the conversion of the fatty ester to the corresponding fatty hydroxamic acid, the alcoholic solution of the latter is recovered for the preparation of the alkali metal hydroxamates. The neutralization reaction can be conveniently carried out by adding a solution of the selected alkali, i.e., hydroxide or lower alkoxide, in a lower alkanol to the organic phase of the reaction mixture. Alternatively, the hydroxamic acid can be recovered as such for further purification treatment prior to neutralization if desired. In the preparation of the ammonium hydroxamate, the hydroxamic acid obtained as aforedescribed can be further reacted with dimethylamine to yield the ammonium salt. The resultant ammonium salt solution can be conveniently stripped in order to recover the salt in solid form.

In order to illustrate the best mode contemplated for carrying out the present invention, the following examples are set forth. As indicated, these examples are given primarily by way of illustration and, accordingly, any enumeration of detail set forth therein is not to be construed as a limitation on the invention except that such limitation is expressed in the appended claims. All parts and percentages are by weight unless otherwise indicated.

EXAMPLE I

This example illustrates the preparation of potassium $C_8 - C_{10}$ hydroxamate.

In a stirred reactor were charged 82 grams hydroxylamine sulfate, 170 grams methyl esters of a mixture of $C_8 - C_{10}$ fatty acids derived from coconut oil and 300 ml. methanol. After stirring until blended, 45 grams dimethylamine were bubbled into the reaction mixture and thereupon the mixture was allowed to stand for about 15 hours. Methanol was then stripped off, leaving a viscous oil (hydroxamic acid + dimethylamine sulfate) which was poured into 62 grams of potassium hydroxide dissolved in 200 ml. of methanol. Immediately, a voluminous white precipitate formed which was filtered off, washed with water and dried. The product was identified by infra-red analysis and found to be potassium $C_8-C_{10}$ hydroxamate. The yield was 180 grams, i.e., about 75% quantitative.

EXAMPLE II

This example illustrates the preparation of dimethyl ammonium $C_8-C_{10}$ hydroxamate.

In a stirred reactor were charged one gram equivalent of hydroxylamine sulfate, one gram mole of methyl esters of a mixture of $C_8-C_{10}$ fatty acids as employed in Example I and 300 ml. methanol. After stirring, two gram moles of dimethylamine are bubbled into the flask after which the mixture is allowed to stand for about 15 hours. Methanol was then stripped off leaving a white solid which is shown to contain dimethyl ammonium $C_8-C_{10}$ hydroxamate by infra-red analysis.

EXAMPLE III

This example further illustrates the preparation of potassium $C_8-C_{10}$ hydroxamate.

In a reactor equipped with stirrer were charged 236 grams hydroxylamine sulfate, 395 grams of the methyl esters of a mixture of $C_8-C_{10}$ fatty acids as used in the previous examples and 800 ml. isopropanol. After stirring until well blended, 325 grams dimethylamine were bubbled into the reactor. Following the addition of the dimethylamine, the reaction mixture was stirred overnight. After 5 days standing, the reaction mixture was analyzed for carbonyl content by infra-red analysis and found to contain hydroxamate carbonyl to the exclusion of carboxylate carbonyl. To the reaction mixture were then added 200 ml. water, with stirring. Two layers formed. The bottom layer, after being stripped of water, weighed 200 grams (80% dimethylamine sulfate).

To the separated upper layer was added a solution of 145 grams of potassium hydroxide dissolved in methanol. The voluminous white precipitate, which immediately formed, was filtered off yielding 410 grams of hydroxamate representing a 76% yield.

What is claimed is:
1. A process for the preparation of an alkali metal salt of a fatty hydroxamic acid which comprises the steps:
   1. reacting an anhydrous slurry of hydroxylamine sulfate and a lower alkanol solution of a lower alkyl ester of a $C_6-C_{26}$ fatty acid with dimethylamine to provide an alcoholic solution of the corresponding fatty hydroxamic acid;
   2. neutralizing the fatty hydroxamic acid of step (1) with a lower alkanol solution of an alkali metal hydroxide or lower alkoxide; and
   3. recovering the resultant fatty hydroxamate.

2. A process in accordance with claim 1 wherein the hydroxylamine sulfate and said ester are reacted in approximately equivalent proportions.

3. A process in accordance with claim 2 wherein the ester reactant is the methyl ester of a mixture of saturated straight-chain $C_8-C_{10}$ fatty acids.

4. A process in accordance with claim 3 wherein the lower alkanol of steps (1) and (2) is methanol.

5. A process for the preparation of ammonium fatty hydroxamates which comprises the steps:
   1. reacting an agitated anhydrous slurry of hydroxylamine sulfate and a lower alkanol solution of a lower alkyl ester of a $C_6-C_{26}$ fatty acid with dimethylamine to provide an alcoholic solution of the ammonium salt of the corresponding fatty hydroxamic acid; and
   2. recovering the resultant ammonium fatty hydroxamate.

6. A process in accordance with claim 5 wherein the hydroxylamine sulfate and said ester are reacted in approximately equivalent proportions to provide the ammonium fatty hydroxamate.

7. A process in accordance with claim 6 wherein the ester reactant is the methyl ester of a mixture of saturated straight-chain $C_8-C_{10}$ fatty acids.

* * * * *